United States Patent
Shelton

(10) Patent No.: US 11,284,940 B2
(45) Date of Patent: Mar. 29, 2022

(54) COMBINED LASER BEAM SPLITTER RETRIEVAL DEVICE

(71) Applicant: Gyrus ACMI, Inc., Southborough, MA (US)

(72) Inventor: Kurt G. Shelton, Bedford, MA (US)

(73) Assignee: Gyrus Acmi, Inc., Westborough, MA (US)

( * ) Notice: Subject to any disclaimer, the term of this patent is extended or adjusted under 35 U.S.C. 154(b) by 307 days.

(21) Appl. No.: 15/792,071

(22) Filed: Oct. 24, 2017

(65) Prior Publication Data

US 2019/0117309 A1 Apr. 25, 2019

(51) Int. Cl.
*A61B 18/22* (2006.01)
*A61B 18/20* (2006.01)
*A61B 18/26* (2006.01)
*A61B 17/221* (2006.01)

(52) U.S. Cl.
CPC .......... *A61B 18/22* (2013.01); *A61B 18/201* (2013.01); *A61B 18/26* (2013.01); *A61B 2017/2212* (2013.01); *A61B 2017/2215* (2013.01); *A61B 2018/2035* (2013.01); *A61B 2018/2205* (2013.01); *A61B 2018/2255* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,396,571 A | * | 3/1995 | Saadatmanesh | G02B 6/2848 385/33 |
| 5,751,869 A | * | 5/1998 | Li | A61B 90/35 385/33 |
| 6,039,747 A | * | 3/2000 | Shturman | A61B 17/320758 606/159 |
| 7,297,154 B2 | * | 11/2007 | Tu | A61B 18/245 128/898 |
| 7,344,528 B1 | | 3/2008 | Tu et al. | |
| 7,727,227 B2 | | 6/2010 | Teague et al. | |
| 7,952,719 B2 | * | 5/2011 | Brennan, III | A61B 5/0066 356/479 |

(Continued)

FOREIGN PATENT DOCUMENTS

| | | |
|---|---|---|
| CN | 102791213 A | 11/2012 |
| CN | 109692039 A | 4/2019 |

(Continued)

OTHER PUBLICATIONS

"Hold like a basket and release like a grasper—NGage Nitinol Stone Extractor" Cook Medical, https://www.cookmedical.com/data/resources/URO-BM-UNG-EN-201309-M3.pdf; 2013, 2 pgs.

(Continued)

*Primary Examiner* — Shirley X Jian
(74) *Attorney, Agent, or Firm* — Schwegman Lundberg & Woessner, P.A.

(57) ABSTRACT

Disclosed herein is a medical device. The medical device includes a sheath, a laser fiber, a basket section, and a laser beam splitter. The laser fiber is configured to extend from an end of the sheath. The basket section includes flexible members. At least a portion of the flexible members are between the sheath and the laser fiber. The laser beam splitter is coupled to the laser fiber.

20 Claims, 5 Drawing Sheets

(56) References Cited

U.S. PATENT DOCUMENTS

| | | | |
|---|---|---|---|
| 8,388,630 B2* | 3/2013 | Teague | A61B 17/221 606/127 |
| 8,452,383 B2* | 5/2013 | Norris | A61B 1/00096 600/478 |
| 2005/0075704 A1 | 4/2005 | Tu et al. | 607/88 |
| 2005/0154378 A1 | 7/2005 | Teague et al. | |
| 2006/0093265 A1* | 5/2006 | Jia | B23K 26/032 385/37 |
| 2010/0113906 A1* | 5/2010 | Marple | A61B 5/0066 600/342 |
| 2015/0272679 A1* | 10/2015 | Wang | A61B 5/0075 606/15 |
| 2016/0302868 A1* | 10/2016 | Nagale | A61B 18/24 |
| 2017/0071664 A1 | 3/2017 | Lim | |

FOREIGN PATENT DOCUMENTS

| | | |
|---|---|---|
| EP | 3476350 A1 | 5/2019 |
| EP | 3476350 B1 | 11/2020 |
| JP | S5623943 A | 3/1981 |
| JP | H11276499 A | 10/1999 |
| JP | 2013513430 A | 4/2013 |
| JP | 2019076702 A | 5/2019 |
| WO | WO-2009/108950 A2 | 9/2009 |
| WO | WO-2011071776 A1 | 6/2011 |

OTHER PUBLICATIONS

"Dakota Nitinol Stone Retrieval Device with OpenSure Handle—Every Detail Matters", Boston Scientific, http://www.bostonscientific.com/content/dam/bostonscientific/uro-wh/portfolio-group/retrieval/dakota/pdfs/Dakota-brochure.pdf; Oct. 2016, 4 pgs.

"European Application Serial No. 18195242.5, Extended European Search Report dated Mar. 20, 2019", 7 pgs.

"European Application Serial No. 18195242.5, Response filed Oct. 29, 2019 to Extended European Search Report dated Mar. 20, 2019", 16 pgs.

"European Application Serial No. 20182955.3, Extended European Search Report dated Oct. 6, 2020", 7 pgs.

"Japanese Application Serial No. 2018-192471, Notification of Reasons for Refusal dated Oct. 26, 2020", w/ English Translation, 8 pgs.

"Japanese Application Serial No. 2018-192471, Response filled Jan. 25, 2021 to Notification of Reasons for Refusal dated Oct. 26, 2020", w/English claims, 7 pgs.

"European Application Serial No. 20182955.3, Response filed May 4, 2021 to Extended European Search Report dated Oct. 6, 2020", 24 pgs.

"Japanese Application Serial No. 2018-192471, Examiners Decision of Final Refusal dated Jun. 14, 2021", w/ english translation, 8 pgs.

"Chinese Application Serial No. 201811137776.2, Office Action dated Dec. 1, 2021", w/English Translation, 18 pgs.

"Japanese Application Serial No. 2018-192471, Response filed Oct. 14, 2021 to Examiners Decision of Final Refusal dated Jun. 14, 2021", w English Claims, 10 pgs.

* cited by examiner

COMBINED LASER BEAM SPLITTER RETRIEVAL DEVICE

BACKGROUND

Field of the Invention

The invention relates to a medical device and more specifically relates to a combined laser beam splitter retrieval device.

Brief Description of Prior Developments

In flexible ureteroscopic laser lithotripsy procedures, laser fibers are brought in close proximity to calculi under direct visualization for the purpose of reducing their size so they can be less traumatically removed from patients. Depending on the physical properties of the calculi and its location in the patient's anatomy, different laser parameter settings are optimal for ablating it. Currently marketed lasers do not deliver less than 0.2 Joules of energy per pulse, or pulse peak powers of less than 5 kW. The procedural consequences of even these lowest settings are that small fragments experience retropulsion, and that tissue can be significantly damaged by it if the laser fiber is too close to it. Retropulsion is the movement of calculi away from the source of energy being used to break them.

The consequences to the patient is that they are exposed to procedures that take the physician longer to manipulate the ureteroscope and laser fiber to maintain close proximity to the calculi fragments, and they are exposed to more tissue injury since each accidental tissue exposure to the laser energy is damaging.

Laser fibers are generally adequately flexible so as not to prevent endoscopes from deflecting enough to access all areas of a kidney. They also generally do not take up so much of the endoscopic working channel so as to restrict irrigation required to keep the field of view clear. For these reasons, laser fibers used in flexible lithotripsy have cores that are generally not larger than 272 µm, with outer diameters in the about 400-500 µm range. At the surface of the fiber, the laser may be about 272 µm in diameter.

The size of a typical calculi treated by flexible ureteroscopic lithotripsy ranges from about 5 to 20 mm in diameter, assuming a sphere. Therefore, physicians deploy a variety of techniques to move the 0.272 mm laser fiber over the surface of the calculi. This can take physicians from 15 minutes to over an hour for the larger calculi. Calculi must be reduced to approximately 3 mm fragments if they will be removed by a retrieval device like a stone retrieval basket, or less than approximately 1.5 mm if they will be left in the patient to be flushed out by the normal anatomical urinary system flushing process. As discussed above, the amount of time that it takes to reduce a calculi to acceptable sizes varies based on the physician's skill at maintaining the laser fiber and endoscope in close proximity to the calculi and its larger fragments, the mechanical properties of the particular stone, and the magnitude of the laser parameters being deployed.

The more energy or peak power being used against a calculi, the more readily it will break into fragments, but the more likely that those fragments will be larger, and experience considerable retropulsion requiring the physician to "chase" them and therefore take longer.

Accordingly, there is a need to provide improved and reliable medical device configurations.

SUMMARY

In accordance with one aspect of the invention, a medical device is disclosed. The medical device includes a sheath, a laser fiber, a basket section, and a laser beam splitter. The laser fiber is configured to extend from an end of the sheath. The basket section includes flexible members. At least a portion of the flexible members are between the sheath and the laser fiber. The laser beam splitter is coupled to the laser fiber.

In accordance with another aspect of the invention, a method is disclosed. A sheath is provided. A laser fiber is extended from an end of the sheath. A basket section is slidably connected between the sheath and the laser fiber. The basket section includes flexible members. At least a portion of the flexible members are between the sheath and the laser fiber. A laser beam splitter is coupled to the laser fiber.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
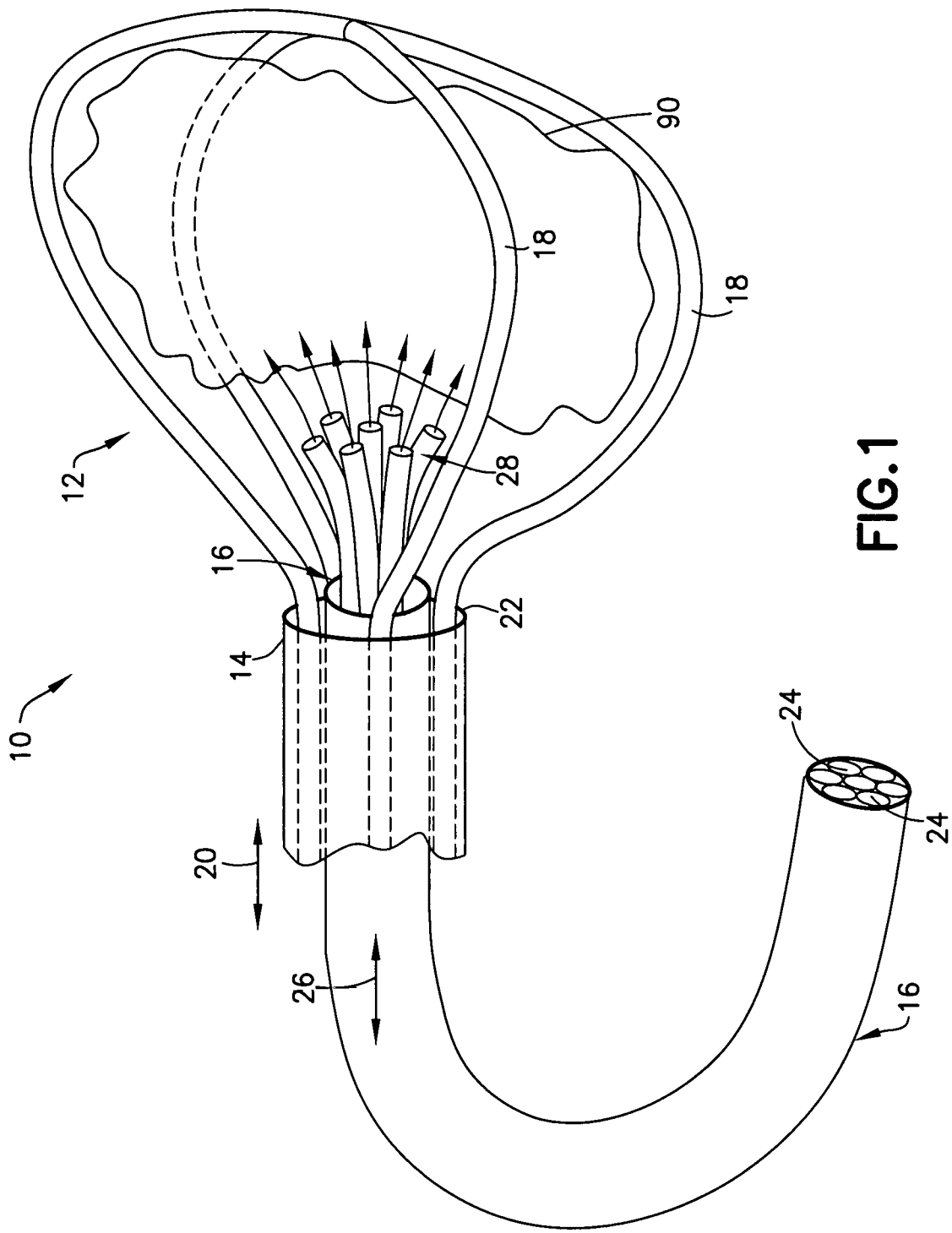
FIG. 1 is a partial section view of a retrieval device incorporating features of the invention.

Referring to FIG. 1, there is shown a partial section view of a retrieval device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The retrieval device 10 comprises a basket section 12, a sheath 14, and a laser fiber 16. The basket section 12 comprises a plurality of flexible members 18 configured to extend from a distal end of the retrieval device 10. The sheath 14 and flexible members 18 are longitudinally movable (see arrow 20) relative to each other to move the basket section between a forward position (to open the basket section 12) and a rearward position (to close the basket section 12) relative to the sheath 14. According to various exemplary embodiments, a control wire for moving the basket section 12 may be connected to ends of the flexible members 18, however in alternate embodiments any suitable configuration for moving the basket section may be provided. FIG. 1 shows the flexible members 18 moved forward relative to the sheath 14 (in the forward position) such that the basket section 12 is open and located out from a front end aperture 22 of the sheath 14. In the rearward position the basket section 12 is located inside the sheath 14 such that the basket section is collapsed (and closed) by the sheath 14 into a smaller shape to fit inside the sheath 14.

Figure 2:
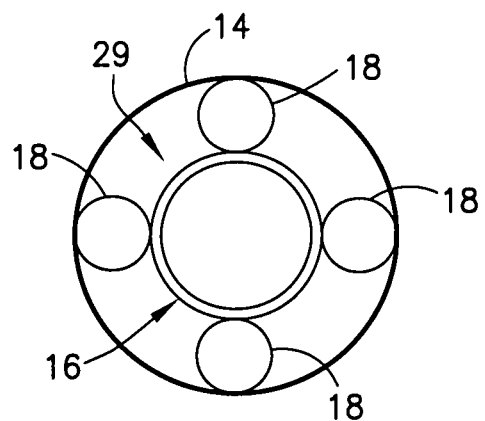
FIG. 2 is a section view through a sheath of the retrieval device shown in FIG. 1.

The laser fiber 16 comprises a plurality of individual core fibers 24 and is configured to extend from the distal end of the retrieval device 10. The laser fiber 16 is longitudinally movable (see arrow 26) relative to the sheath 14 (and the flexible members 18) such that the laser fiber 16 can slide forward and backward. FIG. 1 shows the laser fiber located out from the front end aperture 22 of the sheath 14. The individual core fibers 24 are frayed at the end extending from the aperture 22 and may be fused at an opposite end of the laser fiber. The frayed end 28 of the core fibers allows for the laser beam to be directed in multiple directions. Additionally, the laser fiber 16 is disposed within a channel 29 between the flexible members 18 of the basket section 12 wherein the laser fiber is substantially concentric to the sheath 14 and such that the flexible members 18 are between the laser fiber 16 and the sheath 14 (see FIG. 2). For example, in some exemplary embodiments the diameter of the laser fiber may be about 0.5 mm, the diameter of each of the flexible members may be about 0.104 mm, and the outside diameter of the sheath may be about 1.9-2.0 Fr (wherein the sheath comprises a size and shape of about 1.9-2.0 Fr. catheter [i.e. similar to a catheter having a size 1.9-2.0 on the French scale or French gauge system]). However, in alternate embodiments, any suitably sized laser fiber, flexible members, or sheath may be provided.

Figure 3:
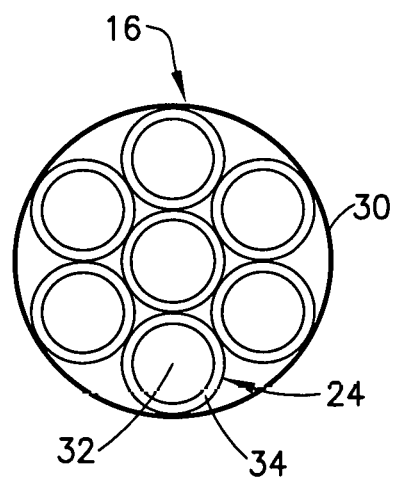
FIG. 3 is a section view through a laser fiber of the retrieval device shown in FIG. 1.

Referring now also to FIG. 3, a section view of the laser fiber 16 is shown. The individual core fibers 24 are bundled within a laser fiber sheath 30 and generally comprise a core portion 32 and a cladding portion 34. According to various exemplary embodiments the diameter of each of the core portions 32 may be about 0.08-0.1 mm. However, in alternate embodiments, any suitably sized core portions may be provided.

Figure 4:
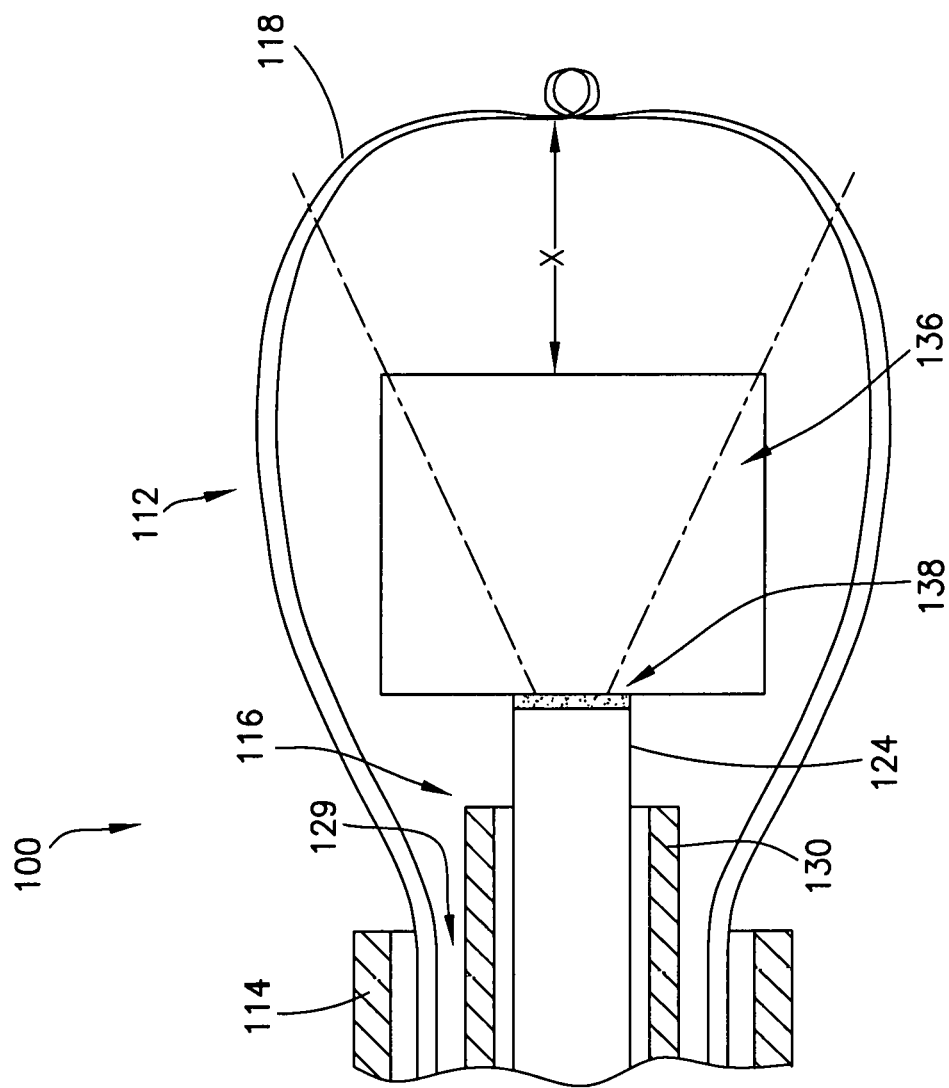
FIG. 4 is another embodiment of a retrieval device incorporating features of the invention.

Referring now also to FIG. 4 another embodiment of a retrieval device is shown. In this embodiment the retrieval device 100 comprises a basket section 112, a sheath 114, and a laser fiber 116, similar to the retrieval device 10 shown in FIG. 1. However in this embodiment, the retrieval device 100 comprises a laser beam diffraction splitter 136. Similar to the retrieval device 10, the basket section 112 comprises a plurality of flexible members 118 configured to extend from a distal end of the retrieval device 10. The sheath 114 and flexible members 118 are longitudinally movable relative to each other to move the basket section between a forward position (to open the basket section 112) and a rearward position (to close the basket section 112) relative to the sheath 114.

FIG. 4 shows one embodiment of a combined nitinol retrieval device and laser fiber with laser beam splitter (or beam spreader) 136 when the retrieval device 100 is closed (with no stone in it). In this embodiment, the beam splitter/spreader 136 has a rectangular profile. When the retrieval device 100 is open, or contains a stone, the basket portion 118 will be extended horizontally such that the space (see dimension X) between the end of the beam splitter/spreader 136 and the distal portion of the retrieval device is larger to capture stone fragments.

In this embodiment, the laser fiber 116 comprises a single core fiber 124 (which may have a diameter of about 0.3 mm, for example) within a laser fiber sheath 130 and is configured to extend from the distal end of the retrieval device 10 (however in alternate embodiments the laser fiber 116 can comprise a bundle of core fibers). The laser fiber 116 is disposed within a channel 129 between the flexible members 118 of the basket section 112 wherein the laser fiber is substantially concentric to the sheath 114 and such that the flexible members 118 are between the laser fiber 116 and the sheath 114. The laser fiber 116 is longitudinally movable relative to the sheath 114 (and the flexible members 118) such that the laser fiber 116 can slide forward and backward. Also, according to some embodiments the laser beam diffraction splitter 136 may have a longitudinal dimension of about 1.2 mm and a perpendicular dimension of about 1.5 mm. However, in alternate embodiments any suitable dimensions may be provided. Additionally, in this embodiment the laser beam diffraction splitter 136 is coupled to the laser fiber 116.

Figure 4C:
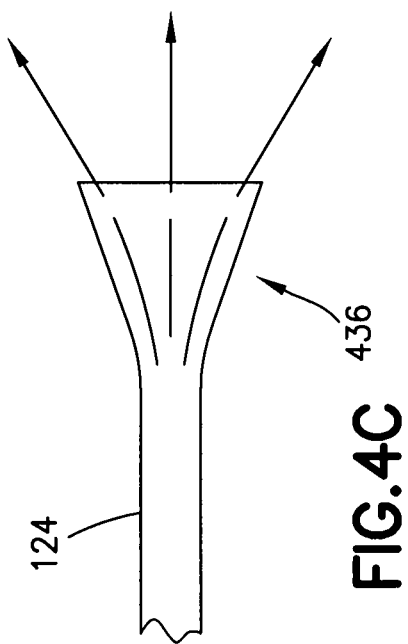
FIGS. 4A-4D are alternate embodiments of a beam spreader of the retrieval device shown in FIG. 4.
Figure 4D:
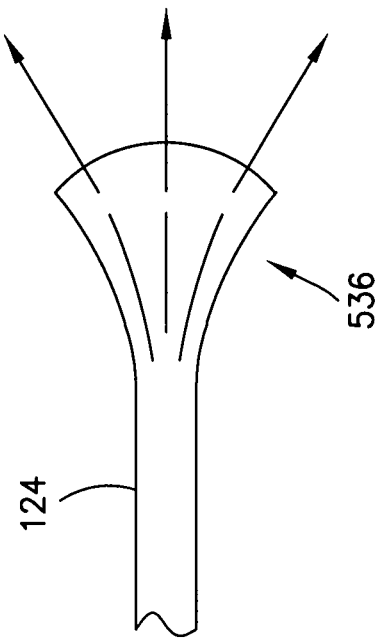
Figure 4A:
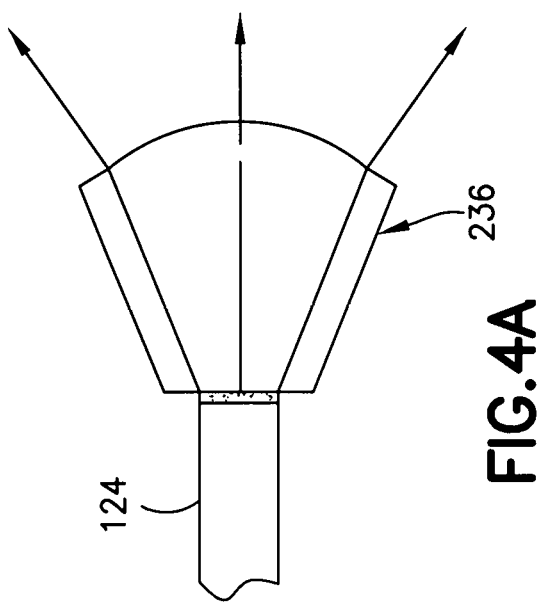
Figure 4B:
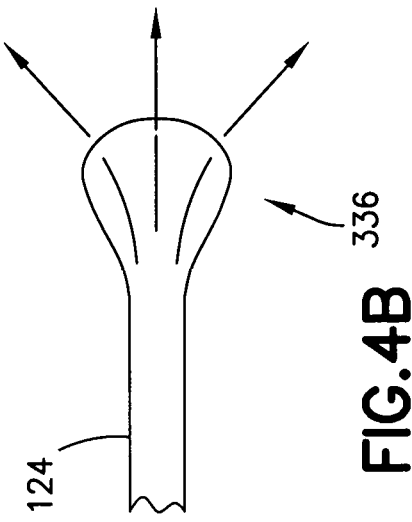

It should be noted that while the embodiment above has been described in connection the beam splitter/spreader 136 having a rectangular profile, one skilled in the art will appreciate that the various embodiments are not necessarily so limited and that in alternate embodiments other suitable profile shapes may be provided. For example, FIG. 4A shows another embodiment wherein the beam splitter/spreader 236 comprises a conical cross section with a rounded end. This configuration can accommodate different shapes of retrieval devices to be captured. FIG. 4B shows another embodiment wherein a beam spreader 336 is formed by creating a rounded bulge at the end of the laser fiber 124 by melting the laser fiber, or joining a half-ball lens to the laser fiber 124. The spherical shape provides for the laser light to spread out over a larger surface area than a straight fiber. Additionally, FIGS. 4C and 4D show beam spreaders 436 and 536 which are similar to the beam spreader 336, however in these embodiments, the beam spreaders comprise either a conical shape at the end of the laser fiber (see FIG. 4C) or a rounded/flared shape at the end of the laser fiber (see FIG. 4D). Furthermore, in other alternate embodiments, any suitable shape may be provided at the end of the laser fiber 124.

As mentioned above, the laser beam diffraction splitter 136 is coupled to the laser fiber 116. It should be noted that the beam splitter/spreader 136 may be attached to the laser fiber core and or cladding using various methods including adhesive with optical transparency for the wavelength under consideration or glass fusion welding or other glass to glass bonding technologies that minimizes the optical minimize transmission losses through the joint so as to minimize the thermal gradient across the joint. In the embodiment shown in FIG. 4, the laser beam diffraction splitter 136 is coupled to the laser fiber 116 by a fusion weld 138.

Figure 5:
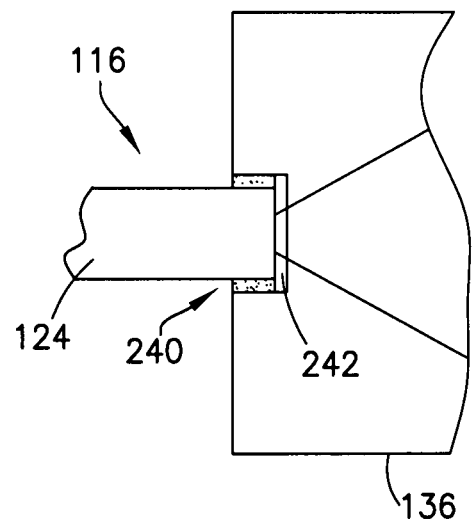
FIG. 5 is an alternate coupling embodiment between a laser fiber and beam spreader of FIG. 4.

It should be noted that while the embodiment above has been described in connection with a fusion weld to couple the laser fiber to the laser beam diffraction splitter, one skilled in the art will appreciate that the various embodiments are not necessarily so limited and that in alternate embodiments other suitable methods of coupling the laser fiber to the laser beam diffraction splitter may be provided. For example, FIG. 5 illustrates an alternate embodiment where a metalized adhesive 240 is provided between the laser fiber and the laser beam diffraction splitter 136. Additionally, a vacuum or other low absorption medium for laser wavelength (about 1940 nm or about 2100 nm) may be provided between the laser fiber and the laser beam diffraction splitter 136.

Technical effects of any one or more of the exemplary embodiments provide significant advantages over conventional configurations by providing the stone retrieval device with a channel for the laser fiber and the laser beam diffraction splitter 136. This configuration supports a captured calculus 90 (as shown in FIG. 1) until the laser energy leaving the fiber either makes a hole in it, or causes it to fragment into two or more pieces. Since the calculus is immobilized by the retrieval device the risk of retropulsion should be significantly diminished or eliminated. However, as mentioned above, a 272 µm or smaller laser fiber is normally moved across the surface of calculi to ablate it. In this configuration, the relative position of the laser fiber and the calculi are maintained by the retrieval device.

The laser beam diffraction splitter (or diffraction beam splitting lens) 136 is provided at the end of the laser fiber 116 (or on the end of a tube protruding from the retrieval device) to address the likely consequence that a single hole of a diameter only slightly larger than the fiber is made in the center of a captured calculus 90. According to various exemplary embodiments, the diffraction beam splitter 136 creates an n×n array of discrete laser beams from one laser beam. The angle of each discrete beam is adjustable by the diffraction properties of the lens and its thickness. In this example, a 10×10 array would split one laser beam into 100 individual beams each delivering the same spatial power density to the stone 90. The duration of each pulse would stay the same, but the peak power of each of the 100 beams would be less than the primary beam, proportional to its surface area. Therefore, if the primary beam delivered, for example, 4 Joules per pulse, then each of the 100 beams could deliver 0.04 Joules per pulse, each having the same pulse duration, but a lower peak power level assuming the target calculi was far enough away from the lens 136 to produce 100 lasers of spot size equal to the primary laser.

With evidence that energies above approximately 0.025 Joules are sufficient to ablate human calculi, additional technical effects of any one or more of the exemplary embodiments are provided. The above beam splitting approach significantly increases the surface area being acted upon and can reduce the need to move a small laser fiber over the surface of a calculus. Additionally, the 10×10 array is just one example, the array size can be tuned to accommodate energy losses due to absorption in the media between the lens surface and a calculi, but still deliver enough intensity to cause ablation.

A further technical effect of any one or more of the exemplary embodiments provides configurations which can better accommodate burn back of the fiber and provide for an improved anti-migration lithotripter.

Figure 6:
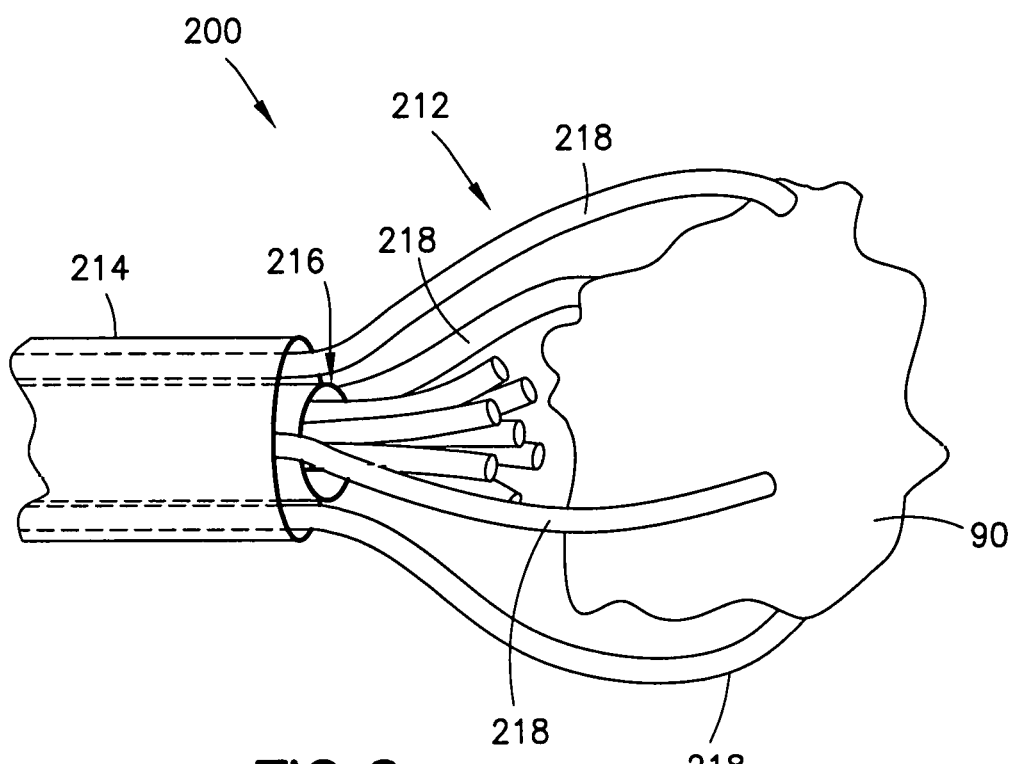
FIG. 6 is an alternate embodiment of a basket section of the retrieval device shown in FIGS. 1, 4.

It should be noted that various exemplary embodiments of the basket section may comprise an open-mouth configuration similar to the NGage® fabricated by Cook Medical, or the Dakota™ fabricated by Boston Scientific, or other retrieval device designs that do not extend all the way around a stone like a snare. For example, as shown in FIG. 6, the retrieval device 200 is similar to the retrieval devices 10, 100 (shown in FIGS. 1, 4) and similarly comprises a basket section 212, a sheath 214, and a laser fiber 216. However, FIG. 6, illustrates the open-mouth configuration mentioned above wherein the flexible members 218 do not extend all the way around the stone 90, and instead provide an open-mouth basket to engage with the stone. It should also be noted that although FIG. 6 shows the laser fiber 216 as having a bundle of core fibers (as in FIG. 1), alternate embodiments may have single core fiber connected to a laser beam diffraction splitter (as in FIG. 4). Additionally, any other suitable laser fiber configuration may be provided.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device is disclosed. The medical device comprises a sheath; a laser fiber configured to extend from an end of the sheath; a basket section comprising flexible members, wherein at least a portion of the flexible members are between the sheath and the laser fiber; and a laser beam splitter coupled to the laser fiber.

A medical device as above wherein the laser fiber is longitudinally movable relative to the sheath.

A medical device as above wherein the laser fiber is substantially concentric with the sheath.

A medical device as above wherein the flexible members are movable relative to the sheath.

A medical device as above wherein the basket section is in an open configuration when the flexible members are moved to a forward position.

A medical device as above wherein the basket section is in a collapsed configuration when the flexible members are moved to a rearward position.

A medical device as above further comprising a channel between the laser fiber and the flexible members, and wherein the laser fiber is movable within the channel.

A medical device as above wherein the laser beam splitter is coupled to the laser fiber by a fusion weld.

A medical device as above wherein the laser beam splitter is coupled to the laser fiber by an adhesive.

A medical device as above wherein the laser fiber and the laser beam splitter are movable relative to the flexible members of the basket device.

In another exemplary embodiment, a method is disclosed. The method comprises providing a sheath; extending a laser fiber from an end of the sheath; slidably connecting a basket section between the sheath and the laser fiber, wherein the basket section comprises flexible members, and wherein at least a portion of the flexible members are between the sheath and the laser fiber; and coupling a laser beam splitter to the laser fiber.

A method as above wherein the laser fiber is longitudinally movable relative to the sheath.

A method as above wherein the laser fiber is substantially concentric with the sheath.

A method as above wherein the flexible members are movable relative to the sheath.

A method as above wherein the basket section is in an open configuration when the flexible members are moved to a forward position.

A method as above wherein the basket section is in a collapsed configuration when the flexible members are moved to a rearward position.

A method as above further comprising a channel between the laser fiber and the flexible members, and wherein the laser fiber is movable within the channel.

A method as above wherein the laser beam splitter is coupled to the laser fiber by a fusion weld.

A method as above wherein the laser beam splitter is coupled to the laser fiber by an adhesive.

A method as above wherein the laser fiber and the laser beam splitter are movable relative to the flexible members of the basket device.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
   a sheath including a proximal end and a distal end;
   a laser fiber including a proximal end and a distal end, the laser fiber configured to extend from the distal end of the sheath and provide a laser beam;
   a basket section comprising flexible members, wherein at least a portion of the flexible members are between the sheath and the laser fiber and are movable relative to the sheath to form a space configured to contain an object; and
   a laser beam splitter coupled to the distal end of the laser fiber and positioned in the basket section, the laser beam splitter structured to create an array of discrete laser beams from the laser beam provided by the laser fiber, the array of discrete laser beams directed distally away from the laser beam splitter;
   wherein the basket section is configured to open and close to capture the object; and
   wherein the device is configured to immobilize the captured object to maintain the relative position of the laser fiber and the object to make a hole in the object or to fragment it into two or more pieces.

2. The medical device of claim 1 wherein the laser fiber is longitudinally movable relative to the sheath.

3. The medical device of claim 1 wherein the laser fiber is substantially concentric with the sheath.

4. The medical device of claim 1 wherein the basket section is in an open configuration to form the space configured to contain the object when the flexible members are moved to a forward position.

5. The medical device of claim 1 wherein the basket section is in a collapsed configuration when the flexible members are moved to a rearward position.

6. The medical device of claim 1 further comprising a channel between the laser fiber and the flexible members, and wherein the laser fiber is movable within the channel.

7. The medical device of claim 1 wherein the laser beam splitter is coupled to the laser fiber by at least one of a fusion weld or an adhesive.

8. The medical device of claim 1 wherein the laser fiber and the laser beam splitter are movable relative to the flexible members of the basket section.

9. A method comprising:
   providing or obtaining a sheath;
   extending a laser fiber from a distal end of the sheath;
   slidably connecting a basket section between the sheath and the laser fiber, wherein the basket section comprises flexible members, and wherein at least a portion of the flexible members are between the sheath and the laser fiber and are movable relative to the sheath to form a space configured to contain an object;
   coupling a laser beam splitter to a distal end of the laser fiber, the laser beam splitter being positioned in the basket section;
   moving the flexible members from a first position to a second position to expand the basket section to an open configuration, thereby forming the space;
   capturing an object in the basket section;
   immobilizing the captured object to maintain the relative position of the laser fiber and the object;
   providing a laser beam through the laser fiber and the laser beam splitter, the laser beam splitter creating an array of discrete laser beams directed distally away from the laser beam splitter and toward the object; and
   using laser energy from the array of discrete laser beams to fragment the object into a plurality of pieces.

10. The method of claim 9 wherein the laser fiber is longitudinally movable relative to the sheath.

11. The method of claim 9 wherein the laser fiber is substantially concentric with the sheath.

12. The method of claim 9 wherein the first position is a rearward position and the second position is a forward position.

13. The method of claim 9 wherein the basket section is in a collapsed configuration when the flexible members are in the rearward position.

14. The method of claim 9 further comprising a channel between the laser fiber and the flexible members, and wherein the laser fiber is movable within the channel.

15. The method of claim 9 wherein the laser beam splitter is coupled to the laser fiber by at least one of a fusion weld or an adhesive.

16. The method of claim 9 wherein the laser fiber and the laser beam splitter are movable relative to the flexible members of the basket device.

17. The medical device of claim 1 wherein the laser beam splitter is configured such that each of the discrete laser beams in the array provides an equal amount of energy to the object.

18. The medical device of claim 1 wherein each of the discrete laser beams in the array has a peak power that is less than a peak power of the laser beam provided through the laser fiber to the laser beam splitter and proportional to a surface area of the discrete laser beam.

19. A medical device comprising:
    a sheath including a proximal end and a distal end;
    a laser fiber including a proximal end and a distal end, the laser fiber configured to extend from the distal end of the sheath and provide a laser beam;
    a basket section comprising flexible members, wherein at least a portion of the flexible members are between the sheath and the laser fiber and are movable relative to the sheath to form a space configured to contain an object; and
    a laser beam splitter coupled directly to the distal end of the laser fiber and positioned in the basket section, the laser beam splitter structured to create an array of discrete laser beams from the laser beam provided by the laser fiber that extend in a forward direction that is oriented distally away from the laser beam splitter;
    wherein the basket section is configured to open and close to capture the object; and
    wherein the device is configured to immobilize the captured object to maintain the relative position of the laser fiber and the object to make a hole in the object or to fragment it into two or more pieces.

20. The medical device of claim 19 wherein each of the discrete laser beams in the array has a peak power that is less than a peak power of the laser beam provided through the laser fiber to the laser beam splitter and proportional to a surface area of the discrete laser beam.

* * * * *